United States Patent [19]
Patel

[11] 4,119,099
[45] Oct. 10, 1978

[54] CATHETER

[75] Inventor: Bhupendra C. Patel, Elgin, Ill.

[73] Assignee: The Kendall Company, Boston, Mass.

[21] Appl. No.: 778,051

[22] Filed: Mar. 16, 1977

Related U.S. Application Data

[63] Continuation-in-part of Ser. No. 745,098, Nov. 26, 1976.

[51] Int. Cl.² .............................................. A61M 25/00
[52] U.S. Cl. ................................................. 128/349 R
[58] Field of Search .............................. 128/348–351, 128/246, 325, 344

[56] References Cited

U.S. PATENT DOCUMENTS

| | | | |
|---|---|---|---|
| 2,912,981 | 11/1959 | Keough | 128/349 B |
| 3,602,228 | 8/1971 | Cowley | 128/349 B |
| 3,742,959 | 12/1971 | Patel | 128/349 B |
| 3,805,794 | 4/1974 | Schlesinger | 128/349 R |

*Primary Examiner*—Dalton L. Truluck

[57] ABSTRACT

A catheter having a shaft including a drainage lumen and an inflation lumen is provided with a molded connector unit bonded to its proximal end, the connector unit including a drainage fitting and an inflation side arm. A rigid adapter tube has its forward end extending into the drainage lumen and its rearward end seated against the drainage fitting to seal the drainage lumen and fitting from the side arm and inflation lumen; the adapter tube provides communication between the drainage lumen and the drainage fitting and the connector unit provides communication between the inflation lumen and the inflation side arm.

9 Claims, 3 Drawing Figures

CATHETER

This application is a continuation-in-part of application Ser. No. 745,098 filed Nov. 26, 1976.

This invention relates to a catheter having a shaft including a drainage lumen and an inflation lumen, and a molded connector unit bonded to the outer surface of the proximal end of the shaft, which connector unit includes a drainage fitting and an inflation side arm communicating with the drainage lumen and inflation lumen respectively.

In one embodiment of the invention, there is provided a rigid adapter tube having its forward end extending into the drainage lumen at the proximal end of the shaft underlying the forward end of the bonded connector unit, and having its rearward end seating against the drainage fitting to seal the drainage lumen and drainage fitting from the inflation side arm and the inflation lumen, said adapter tube providing means for communication between the drainage lumen and the drainage fitting and the connector unit providing means for communication between the inflation lumen and the inflation side arm. In a preferred embodiment of the invention, one of the adapter tube and connector unit includes a projection and the other includes a mating recess for engaging the projection to position the adapter tube with respect to the connector unit and the drainage lumen. The projection may be in the form of an annular rib and the recess in the form of an annular groove; preferably the rib is a radially outwardly extending rib on the adapter tube. It is also preferred that the drainage fitting include a bore through which the adapter tube is insertable to extend into the drainage lumen; in this case, the annular groove is in the wall of the bore. The connector unit may include adjacent its forward end a safety signal balloon overlying and sealed along its margins to the outer surface of the shaft adjacent its proximal end; in this case, the connector unit also provides means for communication between the safety signal balloon and the inflation side arm.

The present invention provides a simple and inexpensive construction, the parts of which can readily be assembled without the need for highly skilled labor.

Figure 1:
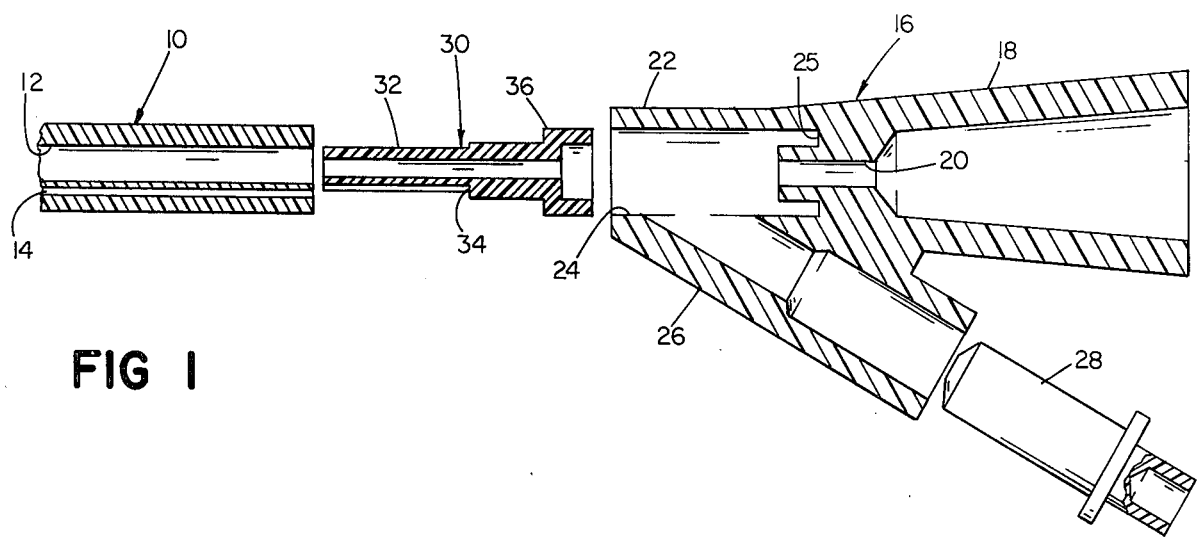
FIG. 1 is a view in section partly broken away showing one embodiment of the present invention prior to asembly.
Figure 2:
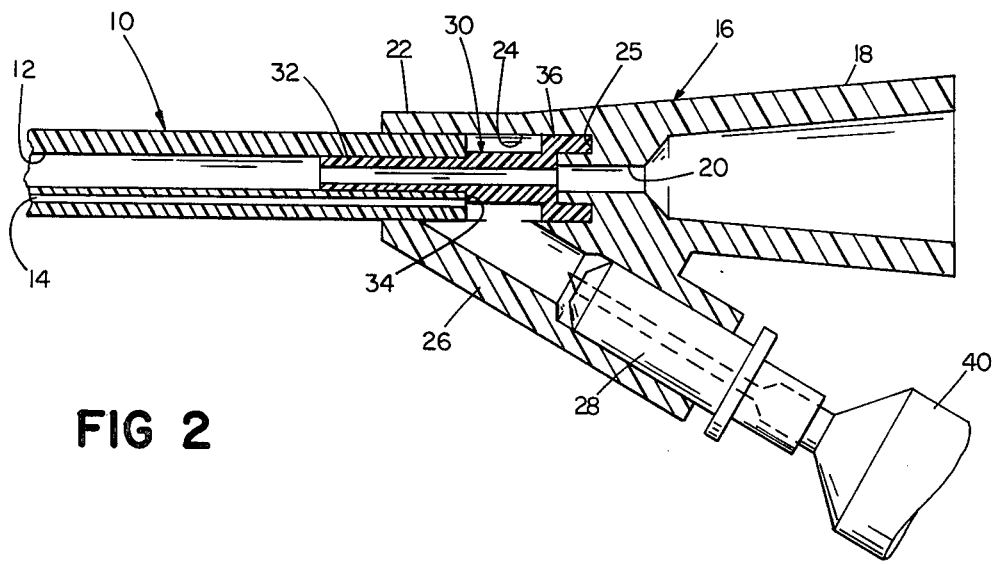
FIG. 2 is a view in section partly broken away showing the embodiment of FIG. 1 in assembled form; and, FIG. 3 is a view in section partly broken away showing another embodiment of the invention in assembled form.

In the drawings, the embodiment shown in FIGS. 1 and 2 includes a conventional catheter shaft 10 having a drainage lumen 12 and an inflation lumen 14. The distal end of shaft 10 (not shown) is of conventional construction adapted to be inserted into a body cavity and having an eye opening to the drainage lumen for collection of fluid from the cavity and having an inflatable retention balloon surrounding the shaft and in communication only with the inflation lumen. Connector unit 16 is of one-piece molded construction and includes drainage fitting 18 having a bore 20 communicating with the forward end 22 of the connector unit which has an aperture 24 of the proper diameter to snugly engage the outer surface of shaft 10. An annular recess 25 in connector unit 16 surrounds the forward end of bore 20. Connector unit 16 also includes inflation side arm 26 which communicates with the aperture 24 in the forward end of the connector unit. Inflation side arm 26 is provided with a combination filling plug and closure 28 at its outer end.

Shaft 10 may be made of any suitable material commonly used for shafts of such catheters while the connector unit 16 can be made of the same material or of any other suitable material having the desired properties, including a natural or synthetic elastomer or a thermoplastic material or a thermoplastic elastomer, preferably a flexible resilient or elastic material.

A rigid adapter tube 30 has a forward end 32 of suitable diameter to fit snugly within drainage lumen 12 at the proximal end of shaft 10. Adapter tube 30 has a shoulder 34 midway along its length which abuts the proximal end of shaft 10 and has at its rearward end a radially outwardly projecting collar or portion of enlarged diameter 36. Collar 36 is of proper diameter to seat snugly in annular recess 25 to seal drainage lumen 12 and drainage fitting 18 together with its bore 20 from inflation side arm 26 and inflation lumen 14. The adapter tube must be relatively rigid for best results and can be made of any suitable hard rigid material such as plastic or metal.

When the shaft, connector unit, and adapter tube are assembled as shown in FIG. 2, the forward end 32 of adapter tube 30 extends into drainage lumen 12, and the forward end 22 of the connector unit overlies and is bonded to the outer surface of shaft 10 adjacent its proximal end. A suitable bond can be achieved either by heat sealing or by means of an appropriate adhesive, depending upon the nature of the materials and the convenience of the manufacturer. Shoulder 34 of the adapter tube seats against the proximal end of shaft 10 and serves, along with forward end 32 of adapter tube 30, to seal the latter to the drainage lumen, while the rearward end of adapter tube 30 seats against the forward end of drainage fitting 18 in recess 25, being held in position by bonding the forward end 22 of the connector unit to the shaft 10. This serves to seal the adapter tube to the drainage fitting, while at the same time sealing both the drainage fitting and the drainage lumen from the inflation side arm and the inflation lumen. Adapter tube 30 provides communication between drainage fitting 18 and drainage lumen 12, while the aperture 24 at the forward end of connector unit 16 provides communication between inflation side arm 26 and inflation lumen 14. In assembling this embodiment the adapter tube is preferably first inserted in the proximal end of the drainage lumen, then the connector unit is passed over it onto the outer surface of the shaft and held fimly in place with the adapter tube seating against the drainage fitting until the bond between the connector unit and shaft has been completed. However, when the wall of the bore 20 is sufficiently flexible and resilient the connector unit can first be bonded to shaft 10 after which the adapter tube is inserted through bore 20 to its desired location.

A hypodermic needle and barrel 40 can be used as the inflating means by passing the needle through valve 28 as shown in FIG. 2.

Figure 3:
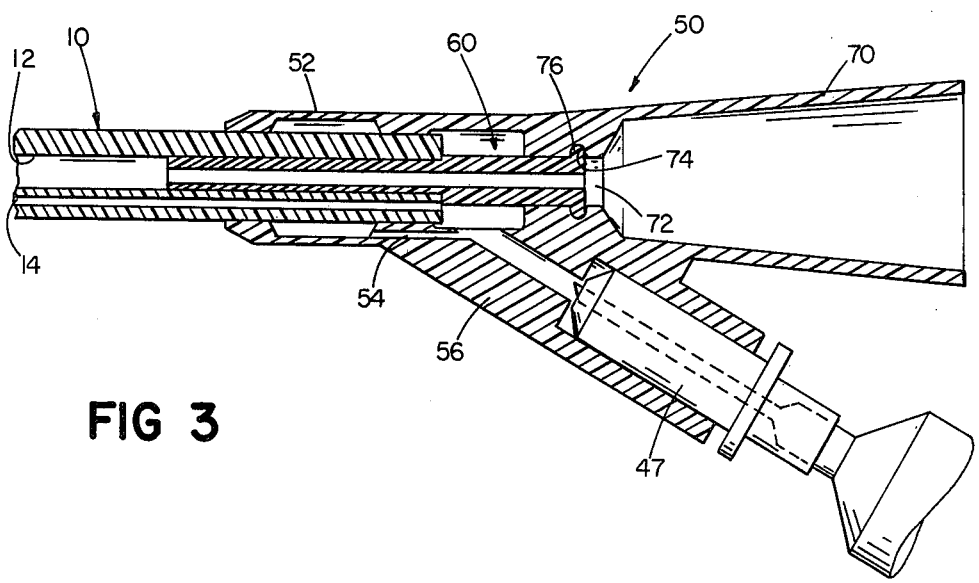

In the embodiment shown in FIG. 3, connector unit 50 includes at its forward or distal end a safety signal balloon 52 which overlies the outer surface of shaft 10 adjacent its proximal end and which is sealed or bonded along its margins to the outer surface of the shaft, using either heat sealing or an adhesive as desired. In this embodiment connector unit 50 includes a supplemental inflation passage 54 extending between inflation side arm 56 and safety signal balloon 52, providing communication therebetween. In this embodiment also, adapter tube 60 has its forward end extending into inflation lumen 12 underlying the forward end of connector unit 50 with the forward end of the adapter tube extending beyond the forward end of the connector unit. Moreover, drainage fitting 70 in this embodiment is provided with a bore 72 sufficiently large so that adapter tube 60 is insertable through it so as to extend into lumen 12. An annular groove 74 is provided in the wall of bore 72 to mate with radially outwardly extending rib 76 on adaptor tube 60 to position the adapter tube properly with respect to the connector unit and the drainage lumen.

In assembling the embodiment of FIG. 3, connector unit 50 can first be mounted on and sealed to the proximal end of shaft 10 after which adaptor tube 60 can be inserted through the drainage fitting to seal the latter and the drainage lumen from the inflation side arm and inflation lumen. In this embodiment the wall of bore 72 is made of a flexible resilient or elastic material to facilitate forcing rib 76 into mating and sealing relation with groove 74.

What is claimed is:

1. In a catheter having a shaft including a drainage lumen and an eye opening communicating therewith at its distal end, and an inflation lumen and a retention balloon communicating therewith, a molded connector unit bonded to the outer surface of said shaft adjacent the proximal end thereof, said connector unit including a drainage fitting having a bore communicating with said drainage lumen and having an inflation side arm, the improvement comprising a rigid adapter tube having its forward end extending into and fitting snugly within said drainage lumen at the proximal end of said shaft underlying the forward end of said bonded connector unit, and having its rearward end seating in sealing engagement against said drainage fitting to seal said drainage lumen and the bore of said drainage fitting from said inflation said arm and inflation lumen, said adapter tube having a bore providing communication between the drainage lumen and the bore of said drainage fitting, and having means separate from both said bores providing in cooperation with said connector unit a means for communication between said inflation lumen and said inflation side arm, one of said adapter tube and said connector unit including a projection and the other including a mating recess for engaging said projection to position said adapter tube with respect to said connector unit and said drainage lumen.

2. A catheter as claimed in claim 1 in which said projection is an annular rib and said recess is an annular groove.

3. A catheter as claimed in claim 2 in which said rib is a radially outwardly extending rib on said adapter tube.

4. A catheter as claimed in claim 1 in which said adapter tube is insertable through said drainage fitting bore to extend into said drainage lumen.

5. A catheter as claimed in claim 1 in which said connector unit includes adjacent its forward end a safety signal balloon overlying and sealed along its margins to the outer surface of said shaft adjacent its proximal end and provides means for communication between said safety signal balloon and said inflation side arm.

6. A catheter as claimed in claim 5 in which said adapter tube is insertable through said drainage fitting bore to extend into said drainage lumen.

7. A catheter as claimed in claim 6 in which said adapter tube includes a radially outwardly projecting rib and said drainage fitting includes in the wall of its said bore an annular mating groove for engaging said rib to position said adapter tube with respect to said connector unit and said drainage lumen.

8. A catheter as claimed in claim 4 in which said drainage fitting bore is smaller in diameter than at least a portion of said adapter tube and is elastically distensible to permit insertion therethrough of said adapter tube.

9. A catheter as claimed in claim 6 in which said drainage fitting bore is smaller in diameter than at least a portion of said adapter tube and is elastically distensible to permit insertion therethrough of said adapter tube.

* * * * *

UNITED STATES PATENT AND TRADEMARK OFFICE
CERTIFICATE OF CORRECTION

PATENT NO. : 4,119,099
DATED : October 10, 1978
INVENTOR(S) : Bhupendra C. Patel It is certified that error appears in the above-identified patent and that said Letters Patent are hereby corrected as shown below:

Column 3, line 42, "said" third occurrence should read --side-

Signed and Sealed this

Sixteenth Day of January 1979

[SEAL]

Attest:

RUTH C. MASON
Attesting Officer

DONALD W. BANNER
Commissioner of Patents and Trademarks